United States Patent [19]
Cocozza

[11] 4,013,075
[45] Mar. 22, 1977

[54] INHALERS AND INSUFFLATORS HAVING A CUTTING MEANS

[75] Inventor: Salvatore Cocozza, Milan, Italy

[73] Assignee: I.S.F. S.p.A., Milan, Italy

[22] Filed: July 15, 1975

[21] Appl. No.: 596,176

[30] Foreign Application Priority Data

July 15, 1975 Italy .................................. 25163/74

[52] U.S. Cl. ................. 128/266; 128/208; 222/193; 222/85
[51] Int. Cl.² ................. A61M 15/06; A61M 15/08
[58] Field of Search .......................... 128/206–210, 128/266, 265; 83/599; 222/85, 82, 86, 193; 131/252, 51

[56] References Cited
UNITED STATES PATENTS

| | | | |
|---|---|---|---|
| 3,906,950 | 9/1975 | Cocozza | 128/266 |
| 3,915,165 | 10/1975 | Rambosek et al. | 128/266 |
| 3,918,451 | 11/1975 | Steil | 128/208 |

FOREIGN PATENTS OR APPLICATIONS 80,696  1/1956  Netherlands ................. 131/252

*Primary Examiner*—Robert W. Michell
*Assistant Examiner*—Henry J. Recla
*Attorney, Agent, or Firm*—Depaoli & O'Brien

[57] ABSTRACT

A device, comprising a detachably connected mouthpiece and body, for powdered substances contained in a capsule which is longitudinally inserted into the cylindrical bore of a pivotably mounted carrier member for pivoting into a transversly disposed recess in the body of the device. A pair of cutting blades is fixedly attached to the body at opposite ends of the recess for severing the ends of the capsule during the pivoting movement. A bore in the mouthpiece and body coincides with the bore of the carrier member and with holes in the blades so that air can be drawn longitudinally through the severed capsule for inhalation or insufflation.

24 Claims, 15 Drawing Figures

INHALERS AND INSUFFLATORS HAVING A CUTTING MEANS

BACKGROUND OF THE INVENTION

1. Field of the Invention

This invention relates to devices for the administration of powdered substances, more particularly for the inhalation and insufflation of powdered medicaments, contained in a capsule.

The invention is more particularly concerned with providing a cutting blade system for the opening of the capsule for releasing the contents, which system is easy to use yet efficient in operation, and is of a compact construction.

2. Review of the Prior Art

In known inhalers and insufflators the opening of the capsule is usually effected by piercing means in the form of pins or drifts of various shapes and dimensions, and the powder is drawn out and mixed with the air which may be directly inhaled by the patient or insufflated by means of a suitable resilient hand-operated pump. In such inhalers and insufflators, the perforations effected by the piercing means in the wall of the gelatine capsule show an irregular fracture of the perforation edges which may cause gelatinous fragments to be present in the substance inhaled or insufflated. Furthermore, the irregular fracture may result in inefficient operation of the device such as non-uniform delivery flows and difficulty in emptying of the capsule.

SUMMARY OF THE INVENTION

The invention aims at obviating the foregoing disadvantages by providing opening means for the capsule which by severing the ends of the capsule ensure a flow of the inhaled or insufflated substance that is substantially free from capsule fragments, operates with constant efficiency, and results in substantially complete emptying of the capsule in a few inhalations or insufflations. The invention also ensures a flow of the powdered substance well mixed with the air, and which easily reaches, for example, the respiratory tract with negligible losses.

Accordingly, in a device for the administration of powdered substances contained in a capsule, the present invention provides a cutting means for opening the capsule in order to release the contents cleanly and completely. The inhaler and insufflator comprise: a generally tubular body having a transverse recess intermediate its ends, a carrier member mounted in the recess for pivotal movement out of and into the recess transversely to the axis of the tubular body and having a cylindrical bore co-axial with the bore of the body for holding a capsule, and a pair of cutting blades, each having a circular aperture and being fixedly mounted in the recess at each end of the bore in the carrier member with the centres of the apertures coinciding with the axes of the bore of the body and of the carrier member. The arrangement is such that, upon pivoting the carrier member containing a capsule into the recess from a position outward thereof, the ends of the capsule are severed by the blades to expose the contents of the capsule to the adjacent cavities of the tubular body. The tubular body may be slightly flared at the entrance of the capsule in order to allow the insertion therein with axial centering.

Preferably, each blade has a cutting edge and the blades are so arranged that the cutting edges face in opposite directions away from one another. Conveniently, one of the pair of blades is disposed adjacent the cavity of the tubular body at one end thereof which constitutes an air inlet, and a grating or sieve member is inserted in the cavity to cover the cavity and to cover the circular aperture in that blade.

The present invention particularly includes an inhalation device, for the administration of powdered substances contained in a capsule, comprising a generally tubular body having a transverse recess intermediate its ends, a carrier member mounted in the recess for pivotal movement out of and into the recess transversely to the axis of the tubular body and having a cylindrical bore co-axial with the body for holding the capsule, and a pair of cutting blades each having a circular aperture and being fixedly mounted in the recess at each end of the bore in the carrier member with the centres of the apertures coinciding with the axis of the bore, one of the blades being disposed adjacent the cavity of the tubular body at one end thereof which constitutes an air inlet and a grating or a sieve member being inserted in the cavity to cover the circular aperture in said one blade, the device further including a mouth-piece secured to the other end of the tubular body, the body and mouth-piece together defining a mixing chamber in which the powdered substance, conveyed by suction at the free end of the mouth-piece from the opened capsule through a diffuser cone in the tubular body, is further mixed with air entering through two radial, diametrically opposite apertures formed in the walls of the mixing chamber.

In order that the invention may be more readily understood, reference is made to the accompanying drawings which illustrate diagrammatically and by way of example two embodiments thereof, and in which.

DESCRIPTION OF THE INHALER

Figure 1:
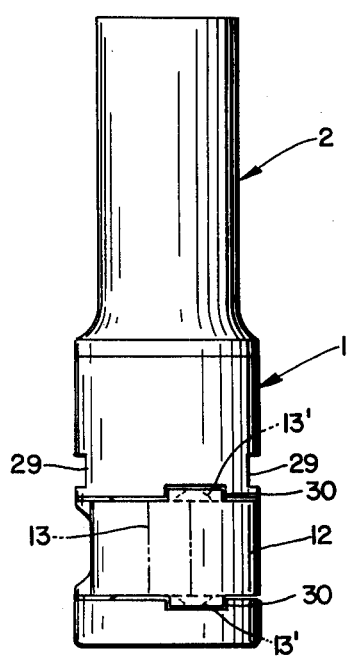
FIG. 1 is a front view of an assembled inhaler with the capsule inserted therein.
Figure 2:
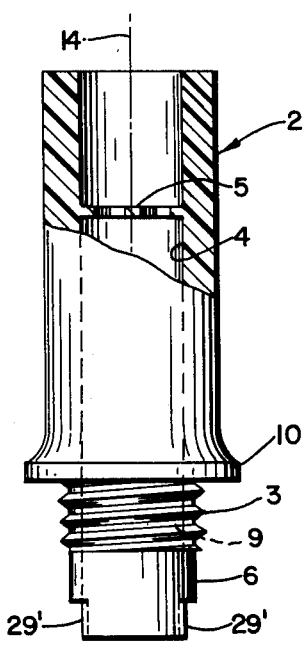
FIG. 2 is a front view and a partial axial section on line A—A of FIG. 3 of the inhaler mouth-piece.
Figure 3:
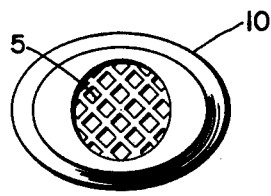
FIG. 3 is a plan view of FIG. 2, taken from the mouth-piece end of the inhaler.
Figure 4:
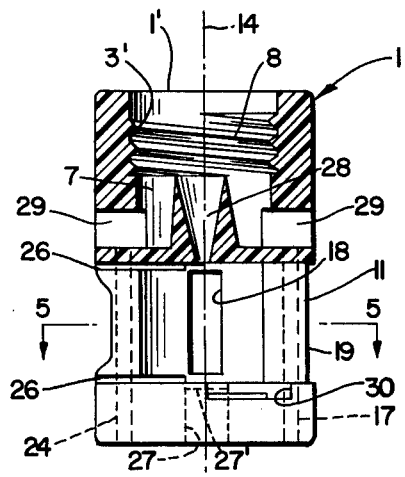
FIG. 4 is an enlarged front view and a partial axial section of the inhaler body.
Figure 5:
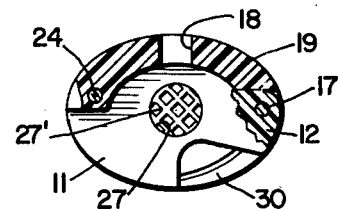
FIG. 5 is a cross-section on the line 5—5 of FIG. 4.
Figure 6:
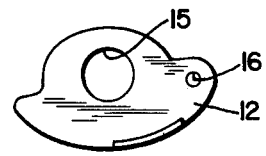
FIG. 6 is a plan view of the carrier member for the capsule.
Figure 7:
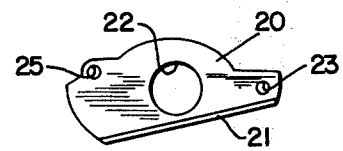
FIGS. 7 and 8 are plan views of the respective cutting blades.
Figure 8:
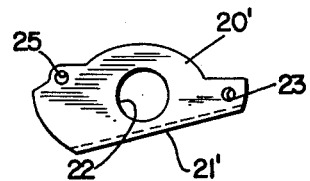

Referring to the drawings, the inhaler illustrated in FIGS. 1 to 8 comprises a generally tubular body 1 and an elongated tubular outlet member or mouth-piece 2 which are releasably connected together end to end by means of complementary screwthreads 3 and 3' provided respectively on the mouth-piece 2 and the body 1. The bore 4 of the mouth-piece 2 is cylindrical and has a fine-mesh grating or gauze 5 inserted therein, close to the free end of the mouth-piece. A stepped spigot portion 6 serves to locate the mouth-piece 2 within a complementarily shaped recess 7 formed in the body 1, inwardly of a space 8 which in conjunction with a portion 9 of the bore 4 forms a mixing chamber, more particularly referred to hereinbelow. An oval-shaped flange 10 on the mouth-piece 2 acts as an abutment for the end face 1' of the body 1.

The body 1 has, intermediate its ends, a transverse recess 11 in which a carrier member 12 for a capsule 13 having hemi-spherical ends 13' is pivotally mounted, with a predetermined end-face clearance, for pivotal movement out of and into the recess 11, transversely to the axis 14 of the body 1 and the mouth-piece 2. The carrier member 12 has a cylindrical bore 15 for holding the capsule 13 and is pivotally mounted at 16 by means of a pin 17 anchored in the body 1. The capsule 13 is inserted into the bore 15 when the member 12 is in a pivoted position out of the recess 11.

The capsule 13 is so dimensioned and is so disposed in the bore 15 that the two hemi-spherical ends 13' project out of the member 12 symmetrically at the ends of the bore 15. A venting aperture 18 is formed in the wall 19 of the recess 11 so as to prevent any air being trapped between the carrier member 12 and the wall 19 when the member 12 is pivoted into the recess 11. In the clearance between each end face of the carrier member 12 and the adjacent end face of the recess 11 there are respectively inserted steel cutting blades 20 and 20'; blade 20 being mounted closer to the mouth-piece 2. Each blade 20, 20' has a singly-bevelled cutting edge 21, 21' and a circular aperture 22 which is concentric with the axis 14, the blades 20, 20' being so arranged that the bevels face in opposite directions away from one another. Each blade 20, 20' is secured in position on the one end by the pin 17 engaging a bearing hole 23 in the blade, and on the other end by a pin 24 anchored in the body 1 and passing through apertures 25 in the blades. Furthermore, in the vicinity of the aperture 25, each blade is received tightly in a recess 26 which is formed in the wall 19 of the recess 11 to enhance the securing of the blades.

At its end opposite that which houses the mixing chamber 8, 9, the body 1 has a co-axial bore 27 which at its inner end adjacent the blade 20' is covered by a grating or perforated wall portion 27' and through which air can be inhaled which then passes through the capsule 13 in order to cause its contents to be drawn out of the capsule and into the mixing chamber 8, 9 via a diffuser cone 28. Two diametrically opposed radial passages 29, which register with correspondingly shaped recesses 29' provided at the free end of the spigot 6 of the mouth-piece 2, are formed in the wall of the body 1 and are in communication via the annular recess 7 with the mixing chamber 8, 9. Upon inhalation, supplementary air is drawn into the mixing chamber 8, 9 through the radial passages 29, 29' and ensures a smooth and uniform flow of the air-powder mixture out of the mixing chamber.

Two radial recesses 30 are also formed in the body 1 at each end of the recess 11 for receiving the severed hemispherical ends 13' of the capsule 13 when the carrier member 12, containing a capsule, is pivoted from a position outside of the recess 11 into the recess 11 in order to expose the contents of the capsule 13 to the adjacent cavities 27 and 28 of the body 1. The body 1 is slightly flared at the entrance of the capsule in order to allow its insertion therein with axial centering.

DESCRIPTION OF HAND-HELD INSUFFLATOR

Figure 9:
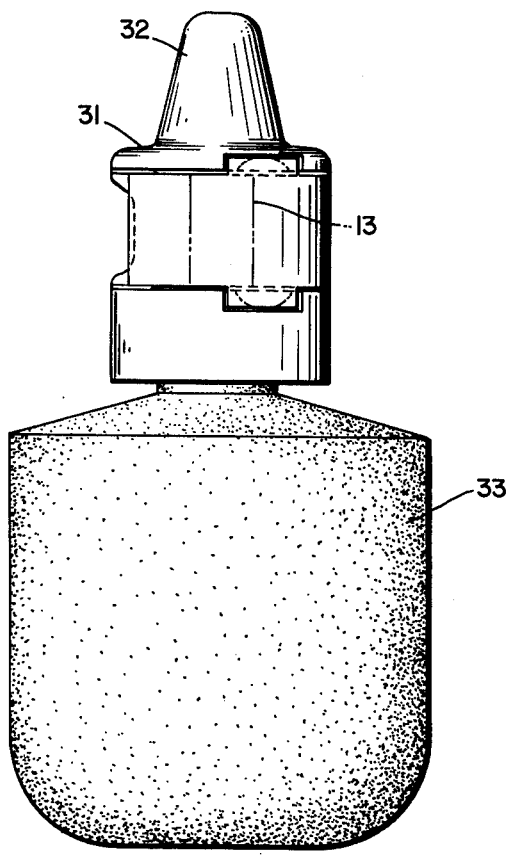
FIG. 9 is a front view of an assembled hand-operated insufflator with the capsule inserted therein.
Figure 10:
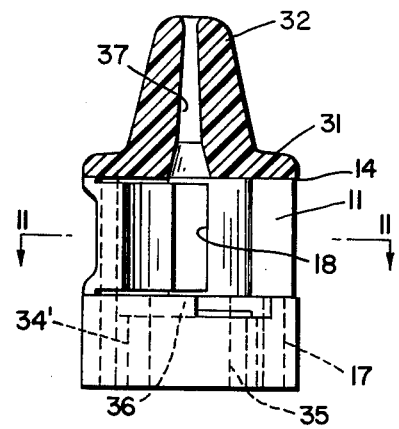
FIG. 10 is an enlarged front view and partial axial section of the hand-operated insufflator body.
Figure 11:
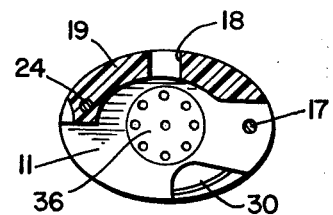
FIG. 11 is a cross-section on line 11—11 of FIG. 10.
Figure 12:
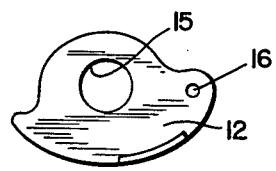
FIGS. 12 to 14 are plan views of the carrier member for the capsule and of the two cutting blades, respectively.
Figure 15:
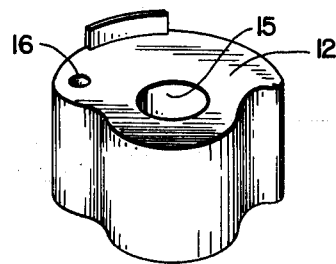
FIG. 15 is a perspective view of the carrier member of FIG. 12.
Figure 13:
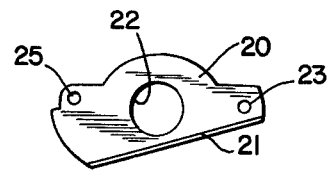
Figure 14:
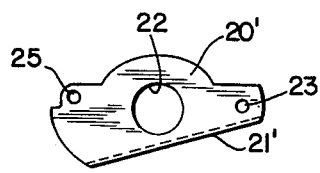

The insufflator illustrated in FIGS. 9 to 14 is particularly suitable for nasal administration of powdered medicaments contained in a capsule. The insufflator comprises two main parts: a generally tubular body 31 having at one end a shaped outlet portion 32, and a resilient, hand-operated bulb pump 33 which is connected by screw-thread means to complementary screw-thread means 34' in the other end of the body 31.

An air inlet chamber 35 is formed in said other end of the body 31 and communicates through an adjacent perforated wall portion 36 with a transverse recess 11 which is formed in the body 31, similar to the recess 11 in the body 1 of the inhaler illustrated in FIGS. 1 to 8. The remainder of the construction of the cutting system for opening the capsule is substantially identical with that of the body 1, and in FIGS. 9 to 14 the same reference numerals have been used to indicate similar elements of the construction. Since in the insufflator the air flow, instead of being produced by inhalation, is produced by the pump, the mixing chamber and the radial passages for the supplementary air are dispensed with. Instead, an outwardly tapering outlet channel 37 is formed in the outlet portion 32. The manner of opening the capsule 13 by the cutting blades is similar to that of the inhaler of FIGS. 1 to 8.

Because it will be readily apparent to those skilled in the art that innumerable variations, modifications, applications, and extensions of these embodiments and principles can be made without departing from the spirit and scope of the invention, what is herein defined as such scope and is desired to be protected should be measured, and the invention should be limited, only by the following claims.

What is claimed is:

1. A device for the administration of a powdered substance contained in a capsule, comprising:
    A. a generally tubular body having a transverse recess intermediate its ends;
    B. a carrier member which is pivotally mounted in said transverse recess for pivotal movement, transversely to the axis of said tubular body, out of and into said transverse recess and having a cylindrical bore co-axial with said body for holding said capsule; and
    C. cutting means for opening said capsule in order to release the contents cleanly and completely, comprising a pair of cutting blades, each having a circular aperture and being fixedly mounted in said recess at each end of the bore in said carrier member with the centres of the apertures coinciding with the axis of said bore, the arrangement being such that upon pivoting the carrier member containing said capsule into said recess from a position outwardly therefrom, the ends of said capsule are severed by said blades to form an opened capsule and expose the contents of said capsule to the adjacent cavities of said tubular body.

2. The device of claim 1 wherein said tubular body is slightly flared to form two radial recesses for positioning said capsule as it enters said transverse recess.

3. The device of claim 1 wherein each said blade has a singly bevelled cutting edge and the blades are so arranged that the bevels of said singly bevelled cutting edges face in opposite directions away from one another.

4. The device of claim 3 wherein said tubular body further comprises a co-axial bore which is aligned with said circular apertures in said blades and wherein one of said blades is disposed adjacent said co-axial bore at one end thereof which constitutes an air inlet, and a grating is positioned transversely of said co-axial bore to cover the circular aperture in said one blade.

5. The device of claim 4 as an inhaler, comprising, in combination, a mouth-piece which is secured end-to-end to the other end of said tubular body, said other end including a recess, said mouth-piece having a bore which is aligned with said co-axial bore and having a stepped spigot portion fitted within said recess in said other end of said tubular body defining a mixing chamber, said recess including radially extending apertures communicating with the surrounding atmosphere and a centrally disposed diffuser cone having an axial bore extending therein, whereby said powdered substance, conveyed by suction from said opened capsule through said diffuser cone in said tubular body, is further mixed with air entering through said apertures formed in the walls of said recess.

6. The device of claim 4 as an insufflator, wherein said tubular body has a shaped outlet portion for nasal administration of powdered medicaments as said powdered substance at one end thereof and a connecting means at the other end thereof, comprising, in combination, said tubular body and a resilient, hand-operated pump having cooperative connecting means which is connected thereby to said other end, said hand-operated pump providing a means for forcing a mixture of said powdered medicaments and of air through said shaped outlet portion.

7. An inhalation device for the administration of a powdered substance contained in a capsule, comprising a generally tubular body having a longitudinally disposed cavity and a transverse recess intermediate its ends, a carrier member which is pivotally mounted in said transverse recess for pivotal movement out of and into the recess transversely to the axis of said tubular body and having a cylindrical bore co-axial with said body for holding the capsule, and a pair of cutting blades, each having a circular aperture and being fixedly mounted in said recess at each end thereof with the centres of the apertures coinciding with the axis of said bore, one of said blades being disposed adjacent said cavity of the tubular body at one end thereof which constitutes an air inlet and a grating being inserted in said cavity and being positioned transversely to said bore and to said cavity to cover the circular aperture in said one blade, the device further including a mouth-piece which is secured end-to-end to the other end of the tubular body, said tubular body, having a recess at said other end, and said mouth-piece, having stepped spigot portion fitted within said recess in said other end of said tubular body, defining a mixing chamber, said recess including radially extending apertures communicating with the surrounding atmosphere and a centrally disposed diffuser cone having an axial bore extending therein, whereby the powdered substance, conveyed by suction at the free end of the mouthpiece from the opened capsule through a diffuser cone in said tubular body, is further mixed with air entering through two radial, diametrically opposite apertures formed in the walls of the mixing chamber.

8. In a device for administration by inhalation or insufflation, including a housing having a bore means for admitting and transmitting a flow of air through a capsule filled with a powdered substance to an administrative outlet, the improvement comprising a cutting means for opening the capsule by severing the ends of the capsule disposed within said bore means and transversely displacing the severed ends of the capsule to form an open-ended tube containing said powdered substance, and thereby admitting and transmitting a flow of air through said open-ended tube for forming an air-powder mixture that is substantially free from capsule fragments and results in substantially complete emptying of said capsule in a few inhalations or insufflations.

9. The device of claim 8, wherein said cutting means comprises a recess in said housing intersecting said bore means, a pair of cutting blades rigidly attached at opposite ends of said recess, transversely to the axis of said bore means, each blade of said pair of cutting blades having a singly-bevelled cutting edge facing in opposite directions and away from said recess.

10. The device of claim 9 wherein each of said blades has a circular aperture which is aligned with said bore means.

11. The device of claim 10 wherein said housing comprises an inlet end and an outlet end, which are connected by said bore means, and wherein said recess is transversely disposed between said ends and has an open side, which interrupts said bore means and at the ends of which said blades are attached so that said cutting edges face toward said open side.

12. The device of claim 11 which further comprises a carrier member which is transversely and pivotably attached to said housing and thereby pivots from an outwardly disposed loading position into said recess, said carrier member comprising a cylindrical bore which is co-axially aligned with said bore means when said carrier member is positioned in said recess and which has a length less than the length of said capsule, said capsule being inserted into said cylindrical bore when said carrier member is in said outwardly disposed loading position, whereby said cutting edges sever protruding ends from said capsule when said carrier member is pivoted into said recess.

13. The device of claim 12, wherein said housing further comprises a venting aperture formed in the wall thereof adjacent to said recess to prevent any air being trapped when said carrier member is pivoted thereinto.

14. The device of claim 13 wherein a radial recess is formed in each said end of said recess for receiving one of said severed ends of said capsule.

15. The device of claim 14 wherein said device is an inhaler and further comprises a mixing chamber which is connected with said bore means downstream of said recess and into which flows a mixture of air and said powdered substance.

16. The inhaler of claim 15 which further comprises two diametrically opposed radial passages which are in communication with said mixing chamber and through which, upon inhalation, supplementary air is drawn into said mixing chamber to ensure a smooth and uniform flow of said mixture out of said mixing chamber.

17. The device of claim 14 wherein said device is an insufflator and further comprises a hand-operated bulb pump which is connected to said bore means at said inlet end and provides said flow of air when operated.

18. The insufflator of claim 17 wherein a shaped outlet portion is attached to said outlet end.

19. The insufflator of claim 18 wherein said outlet portion comprises an outlet channel which tapers toward is outlet and connects with said bore means.

20. An insufflation device for the administration of powdered substances contained in a capsule, comprising a generally tubular body having an inlet end, an outlet end, a longitudinally disposed bore connecting said ends, and a transverse recess intermediate its ends, a carrier member mounted in said recess for pivotal movement out of and into said recess transversely to the axis of said tubular body and having a cylindrical bore for holding the capsule, and a pair of cutting blades, each having a circular aperture and being fixedly mounted in said recess at each end thereof, the axis of bore in said carrier member and the centres of the apertures in said blades coinciding with the axis of said longitudinally disposed bore of said tubular body when said carrier member is positioned in said transverse recess, one of said blades being disposed adjacent the bore of the tubular body at one end thereof which constitutes an air inlet, a grating inserted in said air inlet bore and being positioned transversely to said bore to cover the circular aperture in said one blade, said body having an outlet portion attached to said outlet end, the device further including a resilient, hand-operated pump provided at said inlet end of said tubular body by means of which a mixture of the powdered substance and air can be forced out through said outlet portion.

21. A device for airborne administration of powdered substances contained in a capsule which has a straight portion and a pair of ends, comprising, in combination:

A. a generally tubular body having a longitudinally disposed bore means therewithin;

B. a carrier means for holding said capsule in parallel relationship to said bore means within a storage bore which is as long as said straight portion, whereby said pair of ends stradles said storage bore and are outside thereof;

C. a pair of cutting means, for slicing transversely to said bore means, which are spaced longitudinally apart by a distance equal to said straight portion;

D. a moving means for:

1. moving said capsule past said pair of cutting means, so that said straight portion is severed as an open-ended tube from said pair of ends, and
2. continuing to move said open-ended tube into alignment with said bore means, whereby said powdered substances in said open-ended tube are readily displaced therefrom and entrained by a flow of air through said bore means.

22. The device of claim 21 wherein said body further comprises a retention means for retaining said pair of ends approximately where severed, so that said straight portion and said pair of ends are transversely displaced.

23. The device of claim 22 wherein said body is attached to a mouth-piece having an internal passage to form, in combination, an inhaler wherein said bore means and said internal passage are connected to provide airborne flow of said powdered substances to an administrative outlet in said mouth-piece.

24. The device of claim 22 wherein said body further comprises a shaped outlet portion having an internal passage which is flow-connected to said bore means, said body being further attached to a hand-operated pump to form, in combination, an insufflator wherein said pump provides said flow of air through said bore means, said open-ended tube, and said internal passage.

* * * * *